United States Patent [19]

Zinkosky

[11] Patent Number: 5,240,329
[45] Date of Patent: Aug. 31, 1993

[54] NON-DESTRUCTIVE METHOD FOR DETECTING DEFECTS IN A WORKPIECE

[75] Inventor: Alexander J. Zinkosky, Dearborn, Mich.

[73] Assignee: Ford Motor Company, Dearborn, Mich.

[21] Appl. No.: 929,360

[22] Filed: Aug. 14, 1992

[51] Int. Cl.$^5$ .................. G01N 21/00; G01N 25/72
[52] U.S. Cl. ........................... 374/5; 250/330; 374/169
[58] Field of Search ............... 374/4, 5, 169; 250/330

[56] References Cited

U.S. PATENT DOCUMENTS

| | | |
|---|---|---|
| Re. 32.166 | 6/1986 | Berge . |
| 3,499,153 | 3/1970 | Stanfill, III . |
| 4,636,091 | 1/1987 | Pompei et al. ............ 374/169 X |
| 4,671,674 | 6/1987 | Detronde . |
| 4,768,158 | 8/1988 | Osanai . |
| 4,840,496 | 6/1989 | Elleman et al. ............ 374/124 |
| 4,854,162 | 8/1989 | Yerace et al. . |
| 4,886,370 | 12/1989 | Koshihara et al. . |
| 4,965,451 | 10/1990 | Solter . |
| 4,967,382 | 10/1990 | Hall ................... 374/169 X |
| 4,988,210 | 1/1991 | Koshihara et al. ....... 374/124 X |
| 5,032,727 | 7/1991 | Cox, Jr. et al. ............ 374/4 X |
| 5,052,816 | 10/1991 | Nakamura et al. ........ 374/124 X |

Primary Examiner—Daniel M. Yasich
Attorney, Agent, or Firm—Roger L. May; Joseph W. Malleck

[57] ABSTRACT

A method for detecting defects (10) in a workpiece (12) non-destructively, comprising subjecting the workpiece (12) to a temperature difference in relation to ambient temperature. The method provides an infrared radiometric scanner (14) having a field of view (16) which includes the workpiece (12) being tested, the radiometric scanner (14) sensing an emitted temperature pattern representative of the internal structure (10) of the workpiece (12). The method for detecting defects (10) also communicates a controller (18) with the radiometric scanner (14), the controller (18) receiving an output signal (22) from the radiometric scanner (14) indicative of the emitted temperature pattern before the workpiece (12) is allowed to achieve thermal equilibrium with the ambient environment. The monitor is connected with the controller (18), the monitor being responsive to the output signal (22), whereby the monitor depicts the surface and inner structure of the workpiece so that the workpiece is evaluated for defects (10) in a non-contacting manner.

19 Claims, 3 Drawing Sheets

NON-DESTRUCTIVE METHOD FOR DETECTING DEFECTS IN A WORKPIECE

BACKGROUND OF THE INVENTION

1. Field of the Invention

This invention relates to the art of sensing defects in workpieces and, more particularly, to sensing such defects in thin wall, light metal castings.

2. Related Art Statement

Non-destructive tests are those tests which detect factors related to the serviceability or quality of a part or material without limiting its usefulness. Material defects such as surface cracks, laps, pits, internal inclusions, bursts, shrinking, seams, hot tears, and composition gradients may be detectable, depending on the material and method selected.

Radiation techniques are commonly employed to detect internal discontinuities. Such techniques include, for example, the use of X-rays, or gamma radiation. Gamma radiation is more suitable for field applications than X-ray techniques, since less complex equipment is required. In both methods, radiant energy is passed through the object being examined and is allowed to impinge upon sensitive film. The dark areas on this film are formed by internal defects which absorb less radiation than the sound metal. In general, X-rays are preferred over gamma radiation for laboratory testing since they offer greater control over intensity, and produce sharper pictures.

Inspection and evaluation of the semi-finished product is often necessary. But because semi-finished products may be hot, an observer cannot examine them conveniently. Most approaches presently in use therefore call for forming an image of the weak points or defects at a distance. Such methods may differ both in the means of obtaining the image and in the means of recording this image and using the recording to repair the semi-finished product.

These processes usually require complex equipment and expensive installation. Sometimes, it may be difficult for an observer to distinguish between those points on an image which actually correspond to the state of the semi-finished product and those points resulting from disturbance of the transmission signals issuing from those features. Accordingly, the recording of such images—frequently of low resolution—and the use of such images by the repairer can lead to non-uniform semi-finished products.

Inspection of thin wall light metal castings is presently performed by real time fluoroscopy (X-ray). Fluoroscopic equipment is relatively expensive, requires isolation from employees, occupies significant floor space, requires multiple safety interlocks, consumes a large amount of power, and requires special operator training with federal and state (local in some instances) licensing. Nevertheless, typical fluoroscopic (X-ray) analog image techniques may be partially effective in detecting certain defects. However, if the workpiece has various thicknesses such that its cross-section is non-uniform, multiple images of varying X-ray intensities must be made to detect all defects.

The use of a camera and infrared television to give images of defects is reported in U.S. Pat. No. 4,671,474 at col. 2, lines 6-8. Such techniques produce results which are said to be disturbed by the presence of powders, oxidation spots, and surface irregularities, besides providing little indication of the depth of the defect.

Accordingly, the relatively low resolution of a standard infrared system would be unable to detect small internal defects.

Faced with problems posed by conventional techniques, it would be desirable to have access to a relatively simple process and means for defect detection which produces an image which faithfully portrays defects within a workpiece.

Additionally, it would be desirable to be able to utilize an enhanced, high resolution image which may, for example, be enhanced digitally.

Thus, it would be desirable to be able to use a system, such as an infrared thermographic system for considerably less cost than is associated with, for example, conventional fluoroscopic equipment. Ideally, such a system would not take up an excessive amount of floor space, nor consume excessive power. Finally, it would be useful to be able to position a monitor and controller remotely from the workpiece by the use of suitable cabling. In such a configuration, safety concerns are minimized because such equipment would detect defects by emitted temperature (infrared) radiation with minimal training of the operator.

SUMMARY OF THE INVENTION

To satisfy the above requirements, the present invention discloses a method for detecting defects in a workpiece non-destructively. The method calls for subjecting the workpiece to a temperature difference in relation to the ambient temperature. An infrared radiometric scanner is directed at the workpiece so that the workpiece falls within its field of view. The radiometric scanner senses an emitted temperature pattern which is representative of the thermal structure of the workpiece.

A controller is linked to the radiometric scanner. In use, the controller receives an output signal from the scanner which is indicative of the emitted temperature pattern before the workpiece is allowed to achieve thermal equilibrium with the ambient environment.

To depict the surface and the inner structure of the workpiece for evaluation, a monitor is connected to the controller. The monitor is responsive to the output signal from the radiometric scanner, and may be enhanced digitally.

Using the disclosed method, light metal castings such as a zinc die cast alternator housing can be evaluated non-destructively in a non-contacting manner. Such castings may contain many different kinds of internal defects, such defects including gas bubbles, porosity (round and sponge) and knit lines (which evidence lack of casting integrity). Alternator housings also act as a heat sink which conducts heat away from components such as transistors and diodes which are heat sensitive.

It is known that defects not only lower the component's mechanical strength, but also act as an interference to the flow of heat away from sensitive components. Defects act as thermal barriers and retain heat longer after being heated. Additionally, they stay cold for a longer period of time after being cooled and allowed to return to room temperature. This is because the latent heat of the defect is different than that of the defect-free base material.

BEST MODES FOR CARRYING OUT THE INVENTION

Figure 1:
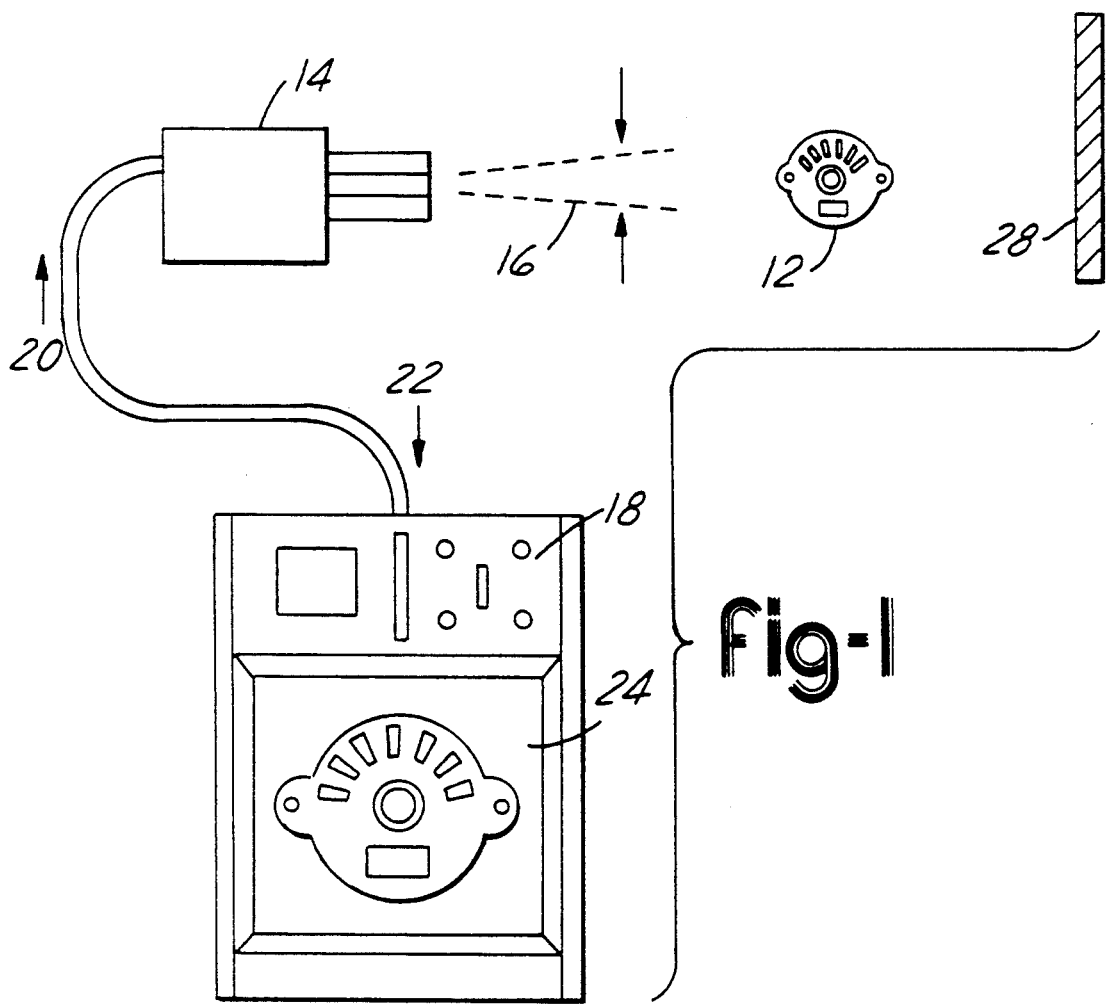
FIG. 1 depicts an apparatus used for detecting defects in a workpiece non-destructively, such apparatus being used to practice the method of the present invention.
Figure 2:
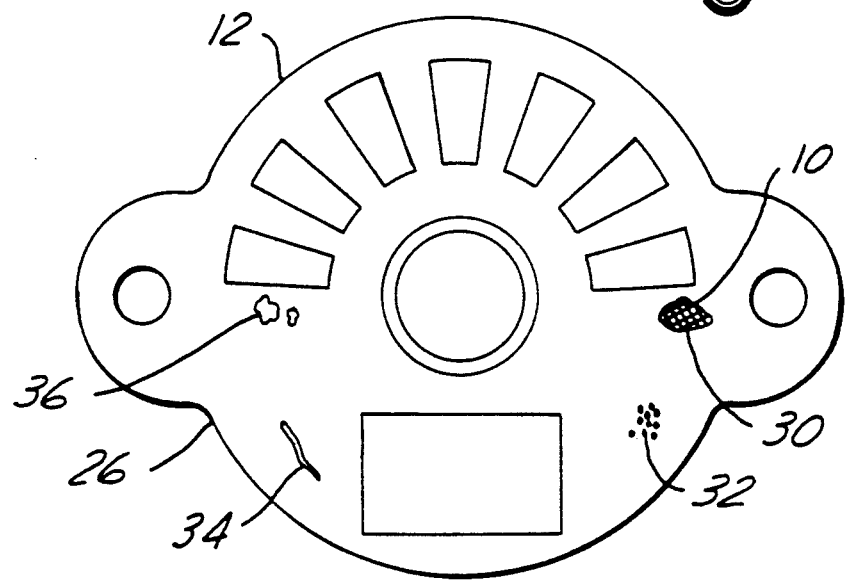
FIG. 2 depicts an image generated by practicing the method of the present invention, the image depicting the size and location of defects within the workpiece.

As shown in FIGS. 1-2, the apparatus used to practice the disclosed method for detecting defects 10 in a workpiece 12 non-destructively comprises the following major components:

an infrared radiometric scanner 14;
a controller 18; and
a monitor 24.

Following the method of the subject invention, the workpiece 12 is first subjected to a temperature difference in relation to ambient temperature, depicted by the reference numeral 28 in FIG. 1. The infrared radiometric scanner 14 is in a position such that its field of view 16 includes the workpiece 12 so that the scanner 14 senses an emitted temperature pattern from the workpiece 12 which is representative of the surface and internal structure thereof. While other devices may be suitable, the infrared radiometric scanner 14 disclosed herein is available from Micron, Model No. TH-1101.

The controller 18 is connected to the radiometric scanner 14, the controller 18 providing an input signal 20 which is indicative of evaluation parameters, such as focal length, aperture, film speed, emissivity, workpiece to scanner distance, ambient air temperature, and optical filter usage (if any). The controller 18 also receives an output signal from the radiometric scanner 14 which is indicative of the emitted temperature pattern existing before the workpiece is allowed to achieve thermal equilibrium with the ambient environment. In use, various controllers 18 may be suitable, but those which have been used to good effect are the Agema 900 series and the Inframetrics Model 760.

Optionally, the controller 18 may include circuitry 19 for digital enhancement. If installed, such circuitry 19 emits signals to the monitor 24 which enables a high resolution infrared image to be displayed.

After the monitor 24 is connected to the controller 18, the monitor 24 is responsive to the output signal 22 from the scanner 14, as enhanced by the controller 18. As a result of the above method steps, the monitor 24 depicts a surface 26 and the internal structure 10 of the workpiece 12 (see, FIG. 2). Though other monitors 24 may be acceptable, one which has been found suitable for use in the disclosed invention is available from Sony Model Super Fine Pitch. In this way, the workpiece 12 is evaluated for defects non-destructively in a non-contacting manner.

Figure 3:
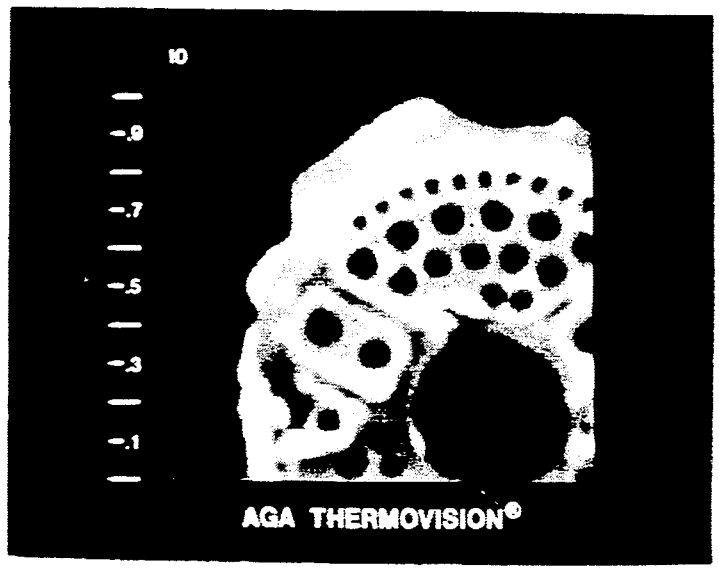
FIG. 3 depicts a conventional analog infrared image.
Figure 4:
FIG. 4 depicts a conventional fluoroscopic (X-ray) analog image.
Figure 5:
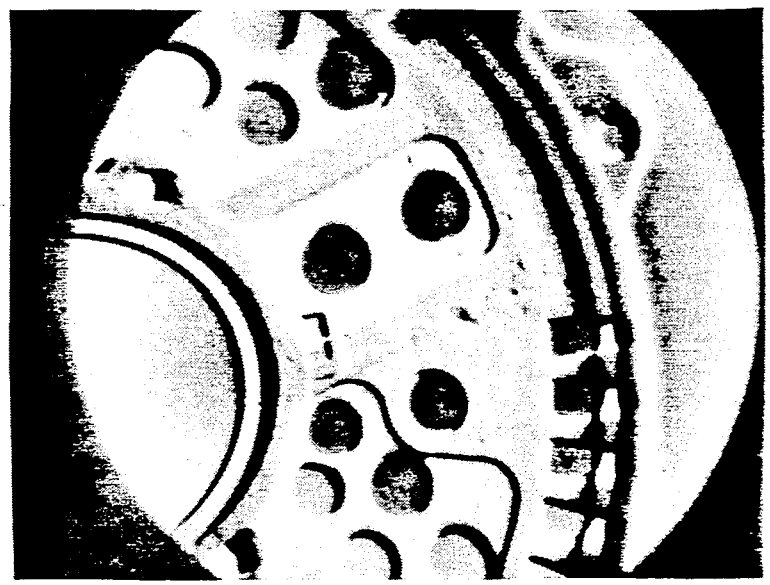
FIG. 5 depicts a digitally enhanced, high resolution infrared image obtained from the method of the present invention.

FIGS. 3-5 represent images available from conventional (FIGS. 3 and 4) and the disclosed (FIG. 5) technique.

FIG. 3 depicts an analog infrared image. While the image may be useful for certain applications (e.g. where the defects are large), the low resolution afforded by a infrared system offers an opportunity for improvement. Such resolution would be unable to detect small internal defects.

FIG. 4 illustrates a typical fluoroscopic (X-ray) analog image. While some defects are detectable, changes in thickness of the workpiece would require multiple images of varying X-ray intensities in order to detect all defects.

FIG. 5, in contrast, depicts a digitally enhanced, high resolution infrared image which is produced following the teachings of the present invention. Digital enhancement circuitry 19 resides within the controller 18. As can be seen from FIG. 5, the clarity of images depicting the defects is somewhat dependent on the size of the defect in relation to the thickness of the specimen and to the proximity of the defect to the surface.

Following the teachings of the disclosed method, real time imaging is available which requires little or no operator training after initial setup and entry of the evaluation parameters. The system is safe because it uses emitted heat radiation, instead of penetrating X-rays.

In use the infrared radiometer 14 views the thin wall casting after the casting is subjected to a temperature difference and before being allowed to equalize to ambient air temperature. Evaluation is begun when the defect displays the greatest temperature difference in relation to the ambient environment 28. Ideally, the workpiece 12 is a light metal casting, which is examined soon after being ejected from a mold. Unless precautions are taken, however, surface oxides, mold release compounds, casting gases, and vapors tend to create false defects or mask existing defects.

Good results from the disclosed method arise when alternator housings are evaluated as they emerge from a simulated hot water/caustic wash. The wash removes casting oxides and mold release compounds, leaving a corrosion-resisting surface. If defect free, that surface exhibits a uniform emissivity. The thin walls and the light metals are efficient thermal conductors and radiators of thermal energy. Such characteristics allow the thin wall castings to show quickly any thermal differences within the internal structure before equalization to room temperature.

Inspection of FIG. 2 reveals the type of defects 10 which are revealed by the disclosed method. Sponge porosity 30 is formed in a higher temperature zone than the surrounding metal and does not have a definite edge. Round gas bubbles 32 also evidence a higher temperature area having a vaguely defined edge. A knit line 34 reveals one side at a higher temperature than the facing side because the knit line 34 impedes conduction. The void 36 is also at a higher retained temperature than the homogeneous casting and has relatively sharply defined extremities.

Thus, there has been disclosed a real time imaging method for non-destructive evaluation of a workpiece in a non-contacting manner which employs emitted heat radiation since temperature differences are associated with discontinuities within a workpiece.

While infrared radiation generally has been disclosed herein, it will be appreciated that short-wave radiation may be particularly suitable for practicing the disclosed method wherein the wavelength may be of the order of 5 microns.

It will be readily apparent to those of ordinary skill in the art that while thin wall die cast structures generally have been disclosed, the disclosed method may be particularly suitable for the non-destructive evaluation of defects in zinc or aluminum castings, or the like.

The method could also be applied to plastics and vitreous materials such as glass windshields, and the quality of components in stealth automobiles. The method could also be used to evaluate adhesive bonding of plastic body panels.

While particular embodiments of the invention have been illustrated and described, it will be obvious to those skilled in the art that various changes and modifications can be made without departing from the invention. It is intended to cover in the appended claims all such modifications and equivalents as fall within the true spirit and scope of the invention.

I claim:

1. A method for detecting defects in a workpiece non-destructively, comprising:
    subjecting the workpiece to a temperature difference in relation to ambient temperature for immersing the workpiece in a hot water/caustic wash for removal of casting oxide and mold release compounds;
    providing an infrared radiometric scanner having a field of view which includes the workpiece being tested, the radiometric scanner sensing an emitted temperature pattern representative of the internal structure of the workpiece;
    connecting a controller with the radiometric scanner, the controller receiving an output signal from the radiometric scanner indicative of the emitted temperature pattern before the workpiece is allowed to achieve thermal equilibrium with the ambient environment; and
    connecting a monitor with the controller, the monitor being responsive to the output signal, whereby the monitor depicts the surface and inner structure of the workpiece so that the workpiece is evaluated for defects in a non-contacting manner.

2. A method for detecting defects in a workpiece non-destructively, comprising:
    subjecting the workpiece to a temperature difference in relation to ambient temperature;
    providing an infrared radiometric scanner having a field of view which includes the workpiece being tested, the radiometric scanner sensing an emitted temperature pattern representative of the internal structure of the workpiece;
    connecting a controller with the radiometric scanner, the controller providing an input signal to the radiometric scanner indicative of evaluation parameters and receiving an output signal from the radiometric scanner indicative of the emitted temperature pattern before the workpiece is allowed to achieve thermal equilibrium with the ambient environment; and
    connecting a monitor with the controller, the monitor being responsive to the output signal from the radiometric scanner, whereby the monitor depicts real time imaging of the surface and inner structure of the workpiece so that the workpiece is evaluated for defects in a noncontacting manner by inspection of a visual image of the structure, the image being generated virtually simultaneously with the time at which the structure is scanned.

3. The method of claim 2, wherein the step of communicating a controller with the radiometric scanner includes the step of digitally enhancing the output signal from the radiometric scanner so that the image depicted by the monitor is a high resolution image.

4. The method of claim 2, wherein the step of subjecting the workpiece to a temperature difference in relation to ambient atmosphere includes the step of immersing the workpiece in a hot water/caustic wash for removal of casting oxide and mold release compounds.

5. A method for detecting defects in a workpiece non-destructively, comprising:
    subjecting the workpiece to a temperature difference in relation to ambient temperature;
    providing an infrared radiometric scanner having a field of view which includes the workpiece being tested, the radiometric scanner sensing an emitted temperature pattern representative of the internal structure of the workpiece;
    connecting a controller with the radiometric scanner, the controller receiving an output signal from the pattern before the workpiece is allowed to achieve thermal equilibrium with the ambient environment; and
    connecting a monitor with the controller, the monitor being responsive to the output signal, whereby the monitor depicts real time imaging of the surface and inner structure of the workpiece so that the workpiece is evaluated for defects in a non-contacting manner by inspection of a visual image of the structure, the image being generated virtually simultaneously with the time at which the structure is scanned.

6. The method of claim 5, wherein the step of connecting a controller with the radiometric scanner includes the step of digitally enhancing the output signal from the radiometric scanner so that the image depicted by the monitor is a high resolution image.

7. The method of claim 5, wherein the step of subjecting the workpiece to a temperature difference in relation to ambient atmosphere includes the step of immersing the workpiece in a hot water/caustic wash for removal of casting oxide and mold release compounds.

8. The method of claim 5, wherein the workpiece is a thin wall casting of aluminum.

9. The method of claim 5, wherein the workpiece is a thin wall casting of zinc.

10. The method of claim 5, wherein the workpiece is a plastic.

11. The method of claim 5, wherein the workpiece is a vitreous material.

12. The method of claim 5, wherein the workpiece is an adhesive bonding between plastic panels.

13. The method of claim 5, wherein the workpiece is an alternator housing.

14. The method of claim 5, wherein the step of providing an infrared radiometric scanner includes the step of utilizing infrared radiation having a wavelength of about 5 microns.

15. An apparatus for detecting defects in a workpiece non-destructively, comprising:
    an infrared radiometric scanner having a field of view which includes a workpiece to be tested,
    the radiometric scanner sensing an emitted temperature pattern between a workpiece having a higher thermal energy than the ambient atmosphere, the emitted temperature pattern being representative of the internal structure of the workpiece;
    a controller connected with the radiometric scanner, the controller receiving an output signal from the radiometric scanner indicative of the emitted temperature pattern before the workpiece is allowed to achieve thermal equilibrium with the ambient environment; and a monitor in communication with the controller, the monitor being responsive to the output signal, whereby the monitor depicts real time imaging of the surface and inner structure of the workpiece so that the workpiece is evaluated for defects in a non-contacting manner by inspection of a visual image of the structure, the image being generated virtually simultaneously with the time at which the structure is scanned.

16. The apparatus of claim 15, wherein the controller further comprises digital enhancement circuitry which receives the output signal from the radiometric scanner and generates a signal for communication to the monitor which provides a high resolution image thereon.

17. A method for detecting defects in a workpiece non-destructively, comprising:

subjecting the workpiece to a temperature difference in relation to ambient temperature by immersing the workpiece in a hot water/caustic wash for removal of casting oxide and mold release compounds;

providing an infrared radiometric scanner having a field of view which includes the workpiece being tested, the radiometric scanner sensing an emitted temperature pattern representative of the internal structure of the workpiece;

connecting a controller with the radiometric scanner, the controller providing an input signal to the radiometric scanner indicative of evaluation parameters and receiving an output signal from the radiometric scanner indicative of the emitted temperature pattern before the workpiece is allowed to achieve thermal equilibrium with the ambient environment; and connecting a monitor with the controller, the monitor being responsive to the output signal from the radiometric scanner, whereby the monitor depicts the surface and inner structure of the workpiece so that the workpiece is evaluated for defects in a non-contacting manner.

18. A method for detecting defects in a workpiece non-destructively, comprising:

subjecting the workpiece to a temperature difference in relation to ambient temperature wherein the material, from which the workpiece is made, and the defects have differing thermal conductivities which affect the emitted temperature pattern which is sensed by the scanner;

providing an infrared radiometric scanner having a field of view which includes the workpiece being tested, the radiometric scanner sensing an emitted temperature pattern representative of the internal structure of the workpiece;

connecting a controller with the radiometric scanner, the controller receiving an output signal from the radiometric scanner indicative of the emitted temperature pattern before the workpiece is allowed to achieve thermal equilibrium with the ambient environment; and connecting a monitor with the controller, the monitor being responsive to the output signal, whereby the monitor depicts real time imaging of the surface and inner structure of the workpiece so that the workpiece is evaluated for defects in a non-contacting manner by inspection of a visual image of the structure, the image being generated virtually simultaneously with the time at which the structure is scanned.

19. The method of claim 18 wherein the workpiece is a thin wall casting of aluminum or zinc, or a plastic material, or a vitreous material, or an adhesive bonding between plastic panels, or an alternator housing.

* * * * *

UNITED STATES PATENT AND TRADEMARK OFFICE
CERTIFICATE OF CORRECTION

PATENT NO. : 5,240,329
DATED : August 31, 1993
INVENTOR(S) : Alexander J. Zinkosky It is certified that error appears in the above-indentified patent and that said Letters Patent is hereby corrected as shown below:

Column 5, line 19, Claim 1, delete "for" and substitute --by--.

Column 5, lines 66-67, Claim 3, delete "communicating" and substitute --connecting--.

Column 6, line 19, Claim 5, before "pattern" insert --radiometric scanner indicative of the emitted temperature--.

Signed and Sealed this

Fifth Day of April, 1994

Attest:

BRUCE LEHMAN

*Attesting Officer*     *Commissioner of Patents and Trademarks*